(12) United States Patent

Hwang

(10) Patent No.: US 12,653,397 B2
(45) Date of Patent: Jun. 16, 2026

(54) SLIT LAMP MICROSCOPE CAPABLE OF IMAGING GOBLET CELLS

(71) Applicant: THE CATHOLIC UNIVERSITY OF KOREA INDUSTRY-ACADEMIC COOPERATION FOUNDATION, Seoul (KR)

(72) Inventor: Hosik Hwang, Seoul (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 333 days.

(21) Appl. No.: 18/481,952

(22) Filed: Oct. 5, 2023

(65) Prior Publication Data

US 2024/0115132 A1 Apr. 11, 2024

(30) Foreign Application Priority Data

Oct. 6, 2022 (KR) ......................... 10-2022-0127518

(51) Int. Cl.
*A61B 3/135* (2006.01)
*A61B 3/14* (2006.01)

(52) U.S. Cl.
CPC ................ *A61B 3/135* (2013.01); *A61B 3/14* (2013.01)

(58) Field of Classification Search
CPC ......... A61B 3/135; A61B 3/14; A61B 3/0008; A61B 3/101

USPC .......................................................... 351/206
See application file for complete search history.

(56) References Cited

U.S. PATENT DOCUMENTS

| | | | | |
|---|---|---|---|---|
| 2010/0129355 A1* | 5/2010 | Ohguro | .............. | C07K 16/2866 |
| | | | | 530/387.3 |
| 2014/0121512 A1* | 5/2014 | Chen | ...................... | A61B 5/414 |
| | | | | 600/431 |
| 2015/0167707 A1* | 6/2015 | Hyers | .................. | F16M 11/041 |
| | | | | 29/446 |
| 2017/0042419 A1* | 2/2017 | Nakanishi | ................ | A61B 3/15 |
| 2018/0035887 A1* | 2/2018 | Nakanishi | .............. | G02B 21/22 |
| 2021/0015363 A1* | 1/2021 | Ohmori | ..................... | A61B 3/15 |
| 2022/0167842 A1* | 6/2022 | Dellagiacoma | .......... | A61B 3/14 |
| 2022/0197057 A1* | 6/2022 | Hwang | .................. | G02C 7/047 |

* cited by examiner

*Primary Examiner* — Mohammed A Hasan

(74) *Attorney, Agent, or Firm* — Knobbe, Martens, Olson & Bear, LLP

(57) ABSTRACT

A slit lamp microscope may include first and second arms rotatably provided on a main shaft; a microscope provided on the first arm and used to observe a subject's eyeball; a light source unit provided on the second arm and irradiating light including near-ultraviolet and visible light regions, including light with a wavelength of 405 nm, to the eyeball of a subject; a third arm rotatably provided on the main shaft; a camera provided on the main shaft and imaging the eyeball of the subject; an excitation filter that transmits only light with a wavelength of 405 nm that induces a fluorescence reaction in stained goblet cells among the light irradiated from the light source unit to the eyeball of the subject; and a light receiving filter that transmits only the light fluorescently reacted in the goblet cells among the light received by the camera.

6 Claims, 5 Drawing Sheets

SLIT LAMP MICROSCOPE CAPABLE OF IMAGING GOBLET CELLS

CROSS-REFERENCE TO RELATED APPLICATION

This application claims priority to and the benefit of Korean Patent Application No. 10-2022-0127518, filed on Oct. 6, 2022, the disclosure of which is incorporated herein by reference in its entirety.

TECHNICAL FIELD

The present disclosure relates to a slit lamp microscope capable of imaging goblet cells, and more particularly, to a slit lamp microscope capable of imaging goblet cells of a subject using a slit lamp.

BACKGROUND

Goblet cells, located in the human eye's conjunctiva, are cells that secrete mucus, a component of tears, and are closely related to eye diseases such as dry eye syndrome.

Therefore, when examining eye diseases, there is a need to observe the state of goblet cells.

Among the methods for examining the condition of the goblet cells, impression cytology is used, and impression cytology is a method of extracting the uppermost cell layer of the conjunctiva by pressing a filter paper into contact with the corneal limbus, staining it, and examining it, and this method causes some damage to the cornea and causes the patient to feel uncomfortable, so other alternatives are required.

In addition, in addition to the above impression cytology, a test method using a confocal reflection microscope has been proposed, but this method also has a disadvantage of being difficult to use, the conjunctival cells do not contrast well with the surrounding cells, and the equipment is expensive, making it difficult to use widely.

In addition, in order to share test results with patients and medical staff, records may need to be recorded through imaging, and the development of equipment that can image goblet cells may be required.

The disclosure of this section is to provide background information relating to the present disclosure. Applicant does not admit that any information contained in this section constitutes prior art.

SUMMARY

The present disclosure is directed to providing a slit lamp microscope for imaging goblet cells using a slit lamp, which is widely used in ophthalmology examination so that a patient's discomfort can be minimized, the goblet cells contrast sharply with the surrounding cells, the goblet cells can be imaged, and the additional cost of examining and imaging the goblet cells is not large.

According to an aspect of the present disclosure, disclosed is a slit lamp microscope capable of imaging goblet cells, including a stand placed on an installation surface; a face holder provided on the stand and on which a subject's head rests; a support base provided on the stand to be movable in a horizontal direction; a main shaft provided on the support base and having a rotation axis in a vertical direction; a first arm rotatably provided on the main shaft; a microscope provided on the first arm and used to observe a subject's eyeball; a second arm rotatably provided on the main shaft; a light source unit provided on the second arm and irradiating light including near-ultraviolet and visible light regions, including light with a wavelength of 405 nm, to the eyeball of a subject; a third arm rotatably provided on the main shaft; a camera provided on the main shaft and imaging the eyeball of the subject; an excitation filter that transmits only light with a wavelength of 405 nm that induces a fluorescence reaction in stained goblet cells among the light irradiated from the light source unit to the eyeball of the subject; and a light receiving filter that transmits only the light fluorescently reacted in the goblet cells among the light received by the camera.

It may further include a mount provided at an end of the third arm and on which the camera is detachably mounted.

It may further include a mount head provided to adjust the angle of the mount.

It may further include a light receiving filter mounting portion provided on the mount head, the angle of which is adjusted together with the camera, and on which the light receiving filter is detachably mounted on the front of the lens of the camera mounted on the mount.

The light receiving filter mounting portion may include a filter boom portion extending from the mount head toward the front direction of the camera; a filter post extending upward from the filter boom portion to a front side of the lens of the camera; and a light receiving filter mounting frame provided at an end of the filter post and on which a light receiving filter is detachably mounted.

The light source may be a white lamp, and an excitation filter mounting portion on which the excitation filter is detachably mounted may be provided on the light emission surface of the light source.

The first arm may include a first boom rotatably coupled to the main shaft and extending in a horizontal direction, and a first post that extends upward from the first boom and is equipped with the microscope, the second arm may include a second boom rotatably coupled to the main shaft higher than the first boom and extending in a horizontal direction, and a second post that extends upward from the second boom and is equipped with the light source unit, and the third arm may include a third boom rotatably coupled to the main shaft higher than the second boom and extending in a horizontal direction, and a third post that extends upward from the third boom and on which the camera is detachably provided, wherein the second boom may be shorter than the first boom, and the third boom may have a shorter length than the second boom.

Advantageous Effects

According to the above configuration, the slit lamp microscope capable of imaging goblet cells according to the present disclosure is a non-invasive method that excludes physical contact with a patient's eyeball and can image goblet cells, minimizing corneal damage and patient discomfort, and can observe goblet cells that are fluorescently excited through staining, so goblet cells can be observed more clearly, and allows observation and imaging using a slit lamp, which is widely used in existing examinations in ophthalmology, so additional costs can be minimized Advantageous effects of the present disclosure are not limited to the above-described effects, and should be understood to include all effects that can be inferred from the configuration of the disclosure described in the detailed description or claims of the present disclosure.

DETAILED DESCRIPTION OF THE EMBODIMENTS

Figure 1:
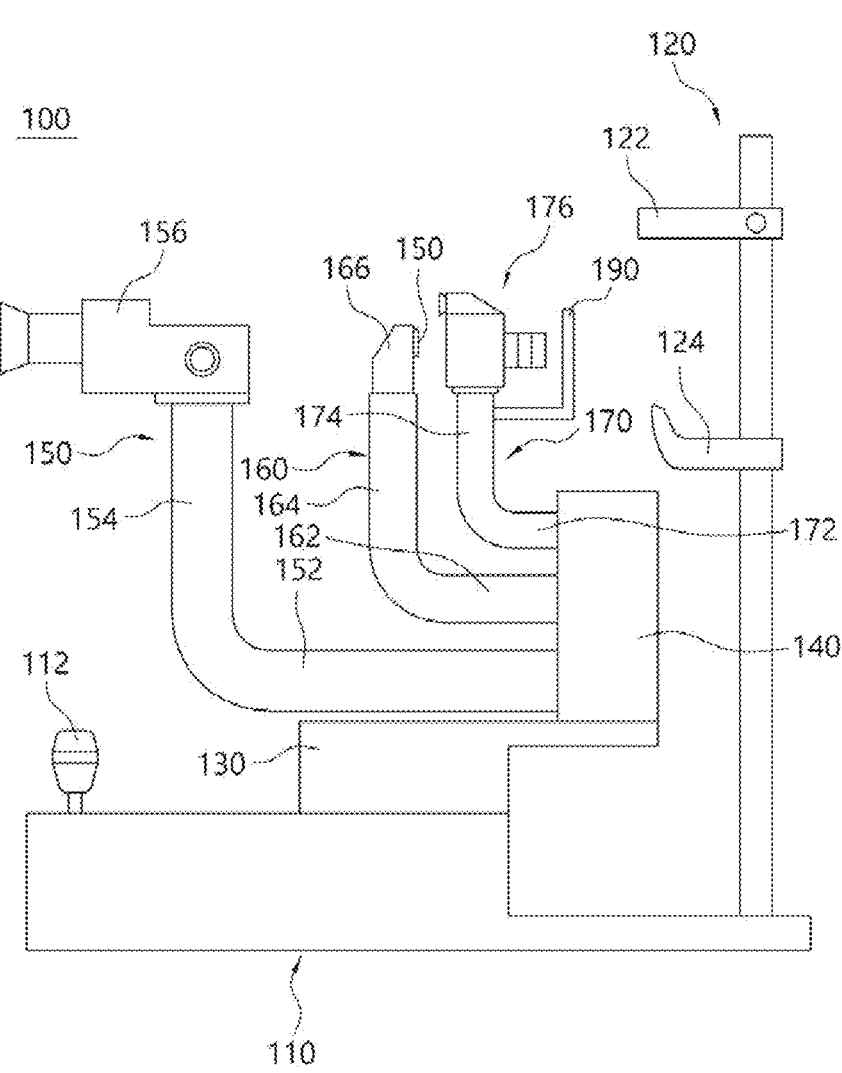
FIG. 1 is a diagram illustrating a slit lamp microscope capable of imaging goblet cells according to an embodiment of the present disclosure.

Hereinafter, embodiments of the present disclosure will be described in detail so that those of ordinary skill in the art can readily implement the present disclosure with reference to the accompanying drawings. The present disclosure may be embodied in many different forms and is not limited to the embodiments set forth herein. In the drawings, parts unrelated to the description are omitted for clarity of description of the present disclosure, and throughout the specification, same or similar reference numerals denote same elements.

Terms and words used in the present specification and claims should not be construed as limited to their usual or dictionary definition, and they should be interpreted as a meaning and concept consistent with the technical idea of the present disclosure based on the principle that inventors may appropriately define the terms and concept in order to describe their own disclosure in the best way.

Accordingly, the embodiments described in the present specification and the configurations shown in the drawings correspond to embodiments of the present disclosure, and do not represent all the technical idea of the present disclosure, so the configurations may have various examples of equivalent and modification that can replace them at the time of filing the present disclosure.

It should be understood that the terms "comprise" or "have" or the like when used in this specification, are intended to describe the presence of stated features, integers, steps, operations, elements, components and/or a combination thereof but not preclude the possibility of the presence or addition of one or more other features, integers, steps, operations, elements, components, or a combination thereof.

The presence of an element in/on "front", "rear", "upper or above or top" or "lower or below or bottom" of another element includes not only being disposed in/on "front", "rear", "upper or above or top" or "lower or below or bottom" directly in contact with other elements, but also cases in which another element being disposed in the middle, unless otherwise specified. In addition, unless otherwise specified, that an element is "connected" to another element includes not only direct connection to each other but also indirect connection to each other.

Hereinafter, a slit lamp microscope capable of imaging goblet cells according to an embodiment of the present disclosure will be described in detail with reference to the drawings.

FIG. 1 is a diagram illustrating a slit lamp microscope 100 capable of imaging goblet cells according to an embodiment of the present disclosure.

The slit lamp microscope 100 capable of imaging goblet cells according to an embodiment of the present disclosure may include a stand 110, a face holder 120, a support base 130, a main shaft 140, a first arm 150, a microscope 156, a second arm 160, a light source unit 166, a third arm 170, a camera 176, an excitation filter 180, and a light receiving filter 190.

The stand 110 may be placed on an installation surface, and may support the loads of the face holder 120, the support base 130, the main shaft 140, the first arm 150, the microscope 156, the second arm 160, the light source unit 166, the third arm 170, the camera 176, the excitation filter 180, and the light receiving filter 190. In this case, the installation surface may be an examination table.

The face holder 120 may be provided so that a subject's head rests on it. The face holder 120 is provided with a chin rest part 124 that supports the subject's chin and a forehead support part 122 that supports the forehead, so that the subject can rest the head by bringing the subject's chin and forehead into close contact.

The support base 130 is mounted on the stand 110 and may be movable in the horizontal direction.

The stand 110 may be equipped with a joystick 112 that can control the movement of the support base 130.

The main shaft 140 is provided at an end of the support base 130 facing the face holder 120, and may have a rotation axis in the vertical direction.

The first arm 150 is rotatably coupled to the main shaft 140, and a microscope 156 for observing the eyeball of a subject may be provided on the first arm 150. The microscope 156 may be equipped to allow an examiner to observe the eyeball of a subject.

The second arm 160 may be rotatably provided on the main shaft 140. In order to avoid interference with the first arm 150, the second arm 160 may be coupled to the main shaft 140 higher than the first arm 150. The second arm 160 may be provided with a light source unit 166 that irradiates light to a subject's eyeball.

The light source unit 166 may be provided to irradiate light including near-ultraviolet and visible light regions, including light with a wavelength of 405 nm, to a subject's eyeball. The light source unit 166 may be a slit lamp. That is, the light source unit 166 may be a slit lamp widely used in eye examinations, and may be light containing light in the 405 nm wavelength band. The light in the 405 nm wavelength band is light in the near-ultraviolet region, and although it belongs to the ultraviolet region, it is close to the visible light region and can reduce the burden on the eyes.

The third arm 170 may be rotatably provided on the main shaft 140. In order to avoid interference with the first arm 150 and the second arm 160, the third arm 170 may be coupled to the main shaft 140 higher than the second arm 160. The third arm 170 may be equipped with a camera 176 that captures fluorescence-excited light from goblet cells of a subject's eyeball.

In addition, it may include an excitation filter 180 and a light receiving filter 190.

The excitation filter 180 may be a filter that transmits only light with a wavelength of 405 nm, which causes a fluorescence reaction in the stained goblet cells, among the light irradiated from the light source unit 166 to the subject's eyeball.

In addition, the light receiving filter 190 is a filter that transmits only the light fluorescently excited in the goblet cells among the light received by the camera 176.

In the present embodiment, as fluoroquinolone-based antibiotics used for staining biological tissues, staining of biological tissues is given as examples of using moxifloxacin, which can be expressed in the near-ultraviolet and visible light regions of autofluorescence.

In addition, in an embodiment of the present disclosure, near-ultraviolet light may mean a wavelength between 405 nm and 478 nm.

That is, after staining the goblet cells of the eyeball conjunctiva, which is the biological tissue to be examined, with the fluoroquinolone-based moxifloxacin, when light containing near-ultraviolet light is irradiated to the stained eye conjunctiva as the light source unit 166, the stained cells may be fluorescently excited.

Therefore, the fluorescently excited goblet cells are observed through the microscope 156 or imaged using the camera 176.

In this case, a light receiving filter 190 configured to transmit only the fluorescently excited light from the goblet cells among the lights received by the camera 176 is detachably provided on the front surface of the camera 176 to image only the fluorescence light to clearly photograph the stained goblet cells.

The first arm 150 may include a first boom 152 rotatably coupled to the main shaft 140 and extending in the horizontal direction, and a first post 154 that extends upward from the first boom 152 and is equipped with the microscope 156.

The second arm 160 may include a second boom 162 rotatably coupled to the main shaft 140 higher than the first boom 152 and extending in the horizontal direction, and a second post 164 that extends upward from the second boom 162 and is equipped with the light source unit 166.

Figure 2:
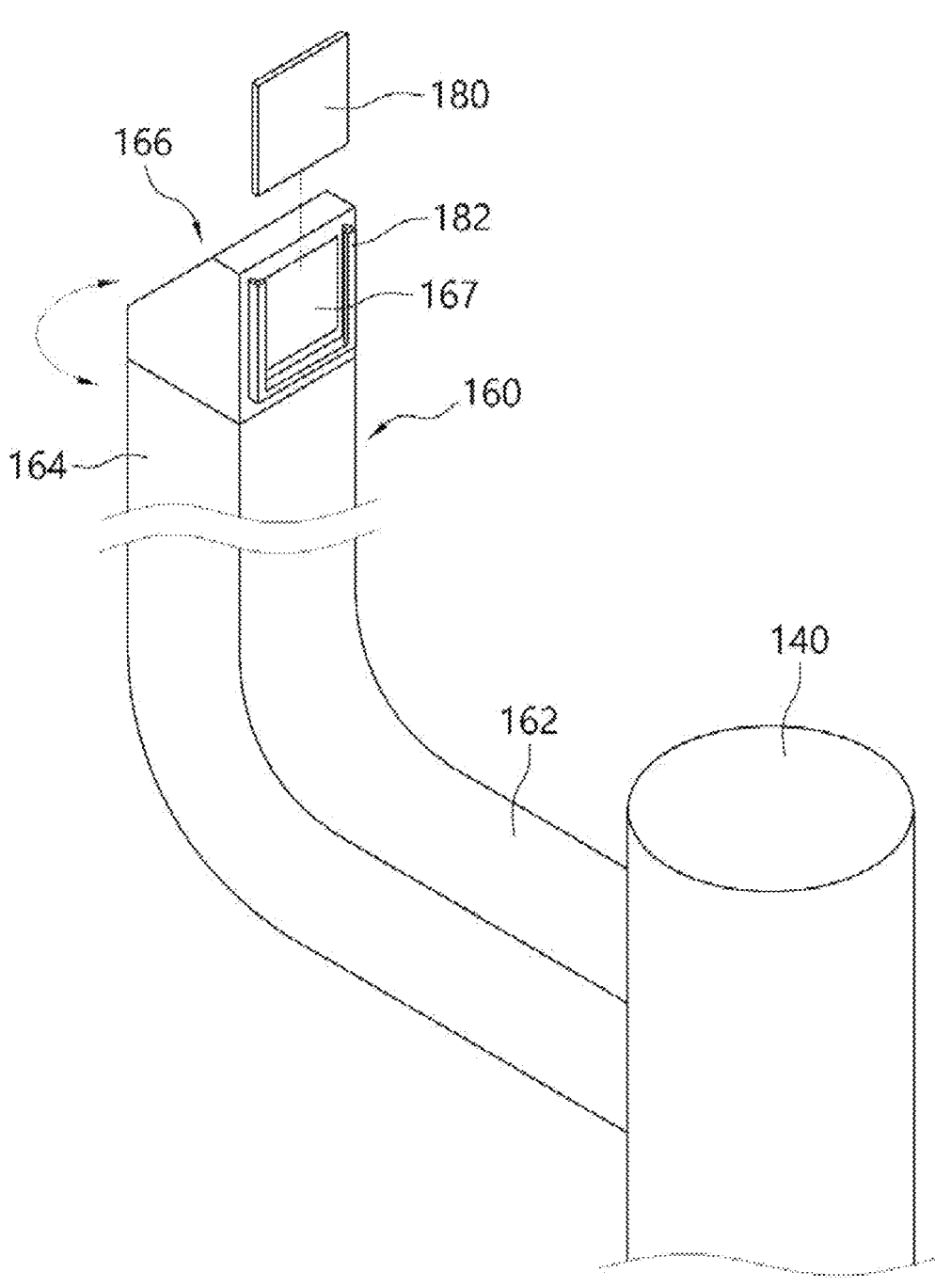
FIG. 2 is a diagram illustrating a second arm and a light source unit according to an embodiment of the present disclosure.

In addition, as shown in FIG. 2, the second post 164 of the second arm 160 may be provided with a light emission surface 167 that emits light. Additionally, an excitation filter mounting portion 182 on which the excitation filter 180 can be mounted on the front of the light emission surface 167 may be provided on the edge of the light emission surface 167. The filter mounting portion may be provided such that a member with a "¬"-shaped cross-section surrounds a side surface and a lower side except the upper side of the edge periphery of the light emission surface 167, and the excitation filter 180 is inserted and mounted between the excitation filter mounting portion 180 and the light emission surface 167.

The third arm 170 may include a third boom 172 rotatably coupled to the main shaft 140 higher than the second boom 162 and extending in the horizontal direction, and a third post 174 that extends upward from the third boom 172 and on which the camera 176 is detachably provided.

In this case, as shown in FIG. 1, the second boom 162 is shorter than the first boom 152, and the third boom 172 has a shorter length than the second boom 162, so that it is possible to avoid the first arm 150, the second arm 160, and the third arm 170 from interfering with each other.

Figure 3:
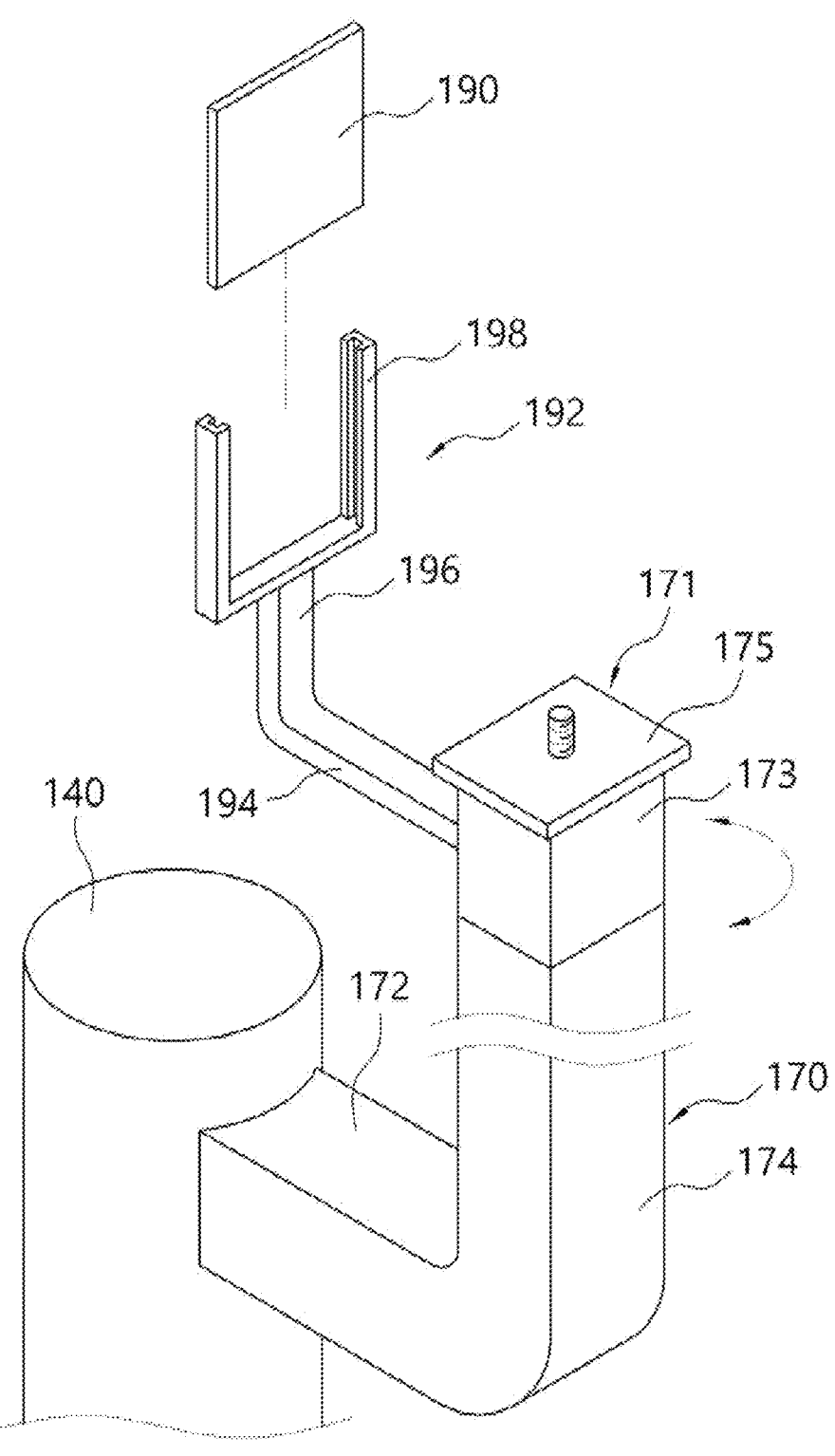
FIG. 3 is a diagram illustrating a third arm and a camera according to an embodiment of the present disclosure.

In addition, as shown in FIG. 3, a mount 175 on which the camera 176 is detachably provided may be provided at the end of the third post 174 of the third arm 170. In addition, a mount head 173 may be provided at the end of the third post 174 to adjust the pitching, yawing, and rolling angles of the mount 175.

That is, the shooting angle of the camera 176 can be adjusted by adjusting the angle of the mount head 173.

Meanwhile, a light receiving filter mounting portion 192 may be provided to detachably mount the light receiving filter 190 to the front of the lens of the camera 176.

The light receiving filter mounting portion 192 is provided on the mount head so that its angle can be adjusted together with the camera 176 mounted on the mount.

As shown in FIG. 3, the light receiving filter mounting portion 192 may include a filter boom 194 portion, a filter post 196, and a light receiving filter mounting frame 198.

The filter boom 194 portion may extend from the mount head toward the front direction of the camera 176.

In this case, the front direction of the camera 176 may refer to the direction in which light is incident on the camera 176.

Additionally, the filter post 196 may be formed to extend upward from the filter boom 194 portion to the front side of the lens of the camera 176. In addition, the light receiving filter mounting frame 198 has a "⊏"-shaped cross-section and is formed to fit around the circumference of the light receiving filter 190, and is provided at the end of the filter post 196, and the light receiving filter 190 may be detachably mounted on the light receiving filter mounting frame.

As described above, the light receiving filter 190 may be provided to transmit only the light band of the excitation light in which the stained goblet cells are excited by light of a near-ultraviolet wavelength and emit fluorescence.

In this case, the light receiving filter mounting frame 198 may be provided so that the light receiving filter 190 is positioned in front of the lens of the camera 176.

That is, the excitation filter 180 is mounted on the light source unit 166, and among the light emitted from the light source unit 166, only the light for fluorescently exciting the stained goblet cells is irradiated to the subject's eyeball, and among the light reflected from the subject's eyeball, only the excited fluorescent light passes through the light receiving filter 190 and the camera 176 captures it.

The slit lamp microscope 100 capable of imaging goblet cells according to an embodiment of the present disclosure may be operated in two modes: an observation mode through an examiner's naked eyes and an imaging mode through the camera 176.

Figure 4:
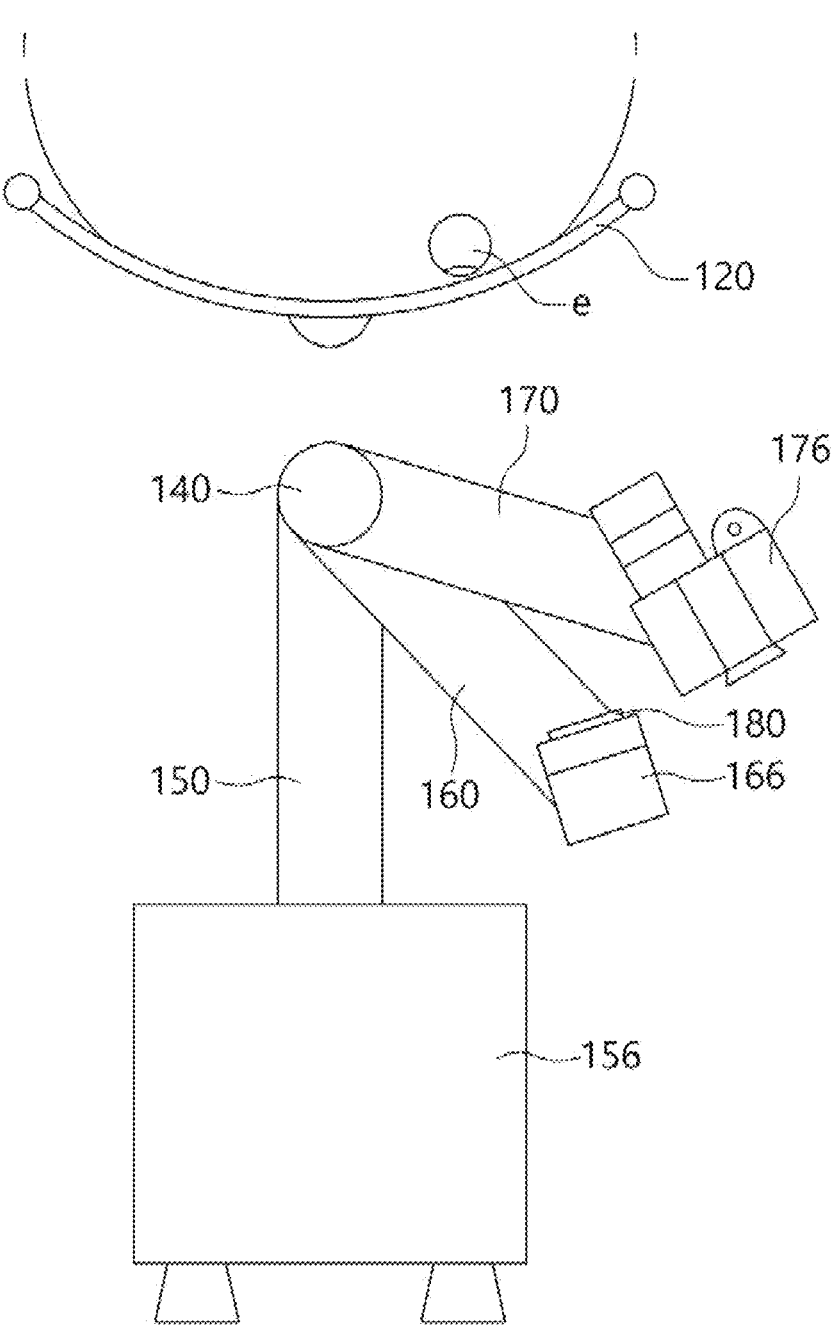
FIG. 4 is a diagram illustrating a slit lamp microscope capable of imaging goblet cells according to an embodiment of the present disclosure when it is in observation mode.

In the observation mode, as shown in FIG. 4, the microscope 156 is positioned to face a subject's eyeball (e), and the third arm 170 may be positioned rotated outward so that the camera 176 does not interfere with the examination.

In this case, the excitation filter 180 and the light receiving filter 190 may not be mounted. Of course, when an examiner wishes to observe goblet cells with the naked eye, the excitation filter 180 may be mounted.

In addition, a separate mounting portion (not shown) on which the light receiving filter 190 may be detachably mounted may be provided on the front portion of the microscope 156, where light enters, so that the light receiving filter 190 may be mounted on the mounting portion of the microscope 156.

Figure 5:
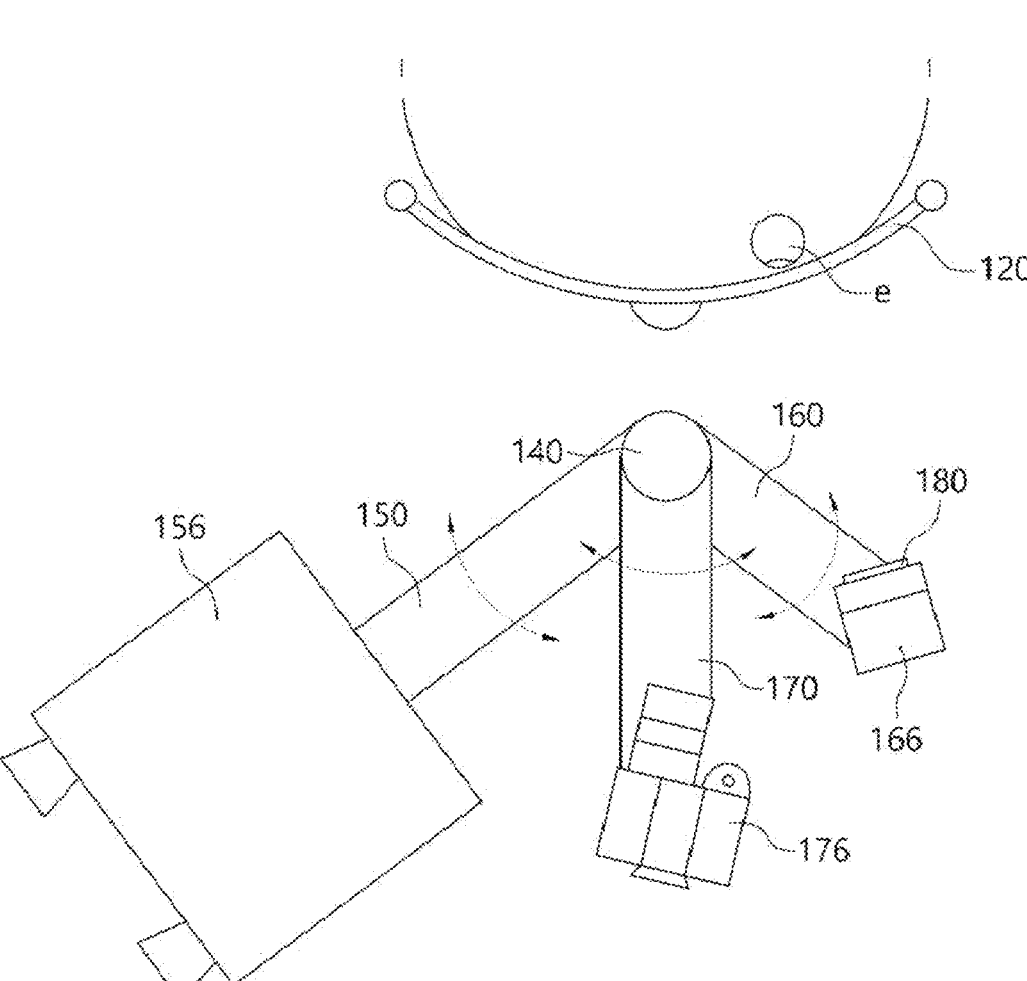
FIG. 5 is a diagram illustrating a slit lamp microscope capable of imaging goblet cells according to an embodiment of the present disclosure when it is in imaging mode.

When the slit lamp microscope 100 capable of imaging goblet cells according to an embodiment of the present disclosure is in the imaging mode, as shown in FIG. 5, the first arm 150 may be positioned rotated outward so that the microscope 156 does not interfere with imaging, and the third arm 170 may be positioned rotated so that the camera 176 faces the subject's eyeball (e).

In this case, the excitation filter 180 and the light receiving filter 190 may be mounted on the excitation filter mounting portion 182 and the light receiving filter mounting portion 192, respectively.

Although embodiments of the present disclosure have been described, the idea of the present disclosure is not limited to the embodiments set forth herein. Those of ordinary skill in the art who understand the idea of the present disclosure may easily propose other embodiments through supplement, change, removal, addition, etc. of elements within the same idea, but the embodiments will be also within the idea scope of the present disclosure.

| <Description of Symbols> | |
| --- | --- |
| 100: slit lamp microscope capable of imaging goblet cells | |
| 110: stand | 120: face holder |
| 130: support base | 140: main shaft |
| 150: first arm | 156: microscope |
| 160: second arm | 166: light source unit |
| 170: third arm | 176: camera |
| 180: excitation filter | 190: light receiving filter |

What is claimed is:

1. A slit lamp microscope configured for capturing fluorescence images of conjunctival goblet cells, comprising:

a stand placed on an installation surface;

a face holder placed over the stand and on which a subject's head rests;

a support base placed over the stand to be movable in a horizontal direction;

a main shaft placed over the support base and having a rotation axis in a vertical direction;

a first arm, a second arm, and a third arm, wherein each of the first arm, the second arm, and the third arm is independently and rotatably coupled to the main shaft in a coaxial arrangement about the rotation axis;

a microscope coupled to the first arm and used to observe a subject's eyeball;

a light source unit coupled to the second arm and configured to irradiate light including near-ultraviolet and visible light regions, including light with a wavelength of 405 nm, to the eyeball of a subject;

a camera coupled to the third arm and configured to capture an image of the eyeball of the subject;

the third arm comprising a mount head;

a filter boom portion extending from the mount head toward a front direction of the camera;

a filter post extending upward from the filter boom portion to a front side of the lens of the camera;

an excitation filter configured to transmit only light with a wavelength of 405 nm that induces a fluorescence reaction in stained conjunctival goblet cells among the light irradiated from the light source unit to the eyeball of the subject; and a light receiving filter mounted on the filter post and configured to transmit only the light fluorescently reacted in the goblet cells.

2. The slit lamp microscope configured for capturing fluorescence images of conjunctival goblet cells of claim 1, further comprising a mount coupled to an end of the third arm, wherein the camera is detachably mounted on the mount.

3. The slit lamp microscope configured for capturing fluorescence images of conjunctival goblet cells of claim 2, wherein the mount head is configured to adjust an angle of the mount.

4. The slit lamp microscope configured for capturing fluorescence images of conjunctival goblet cells of claim 1, further comprising:

a light receiving filter mounting frame disposed at an end of the filter post and on which the light receiving filter is detachably mounted.

5. The slit lamp microscope configured for capturing fluorescence images of conjunctival goblet cells of claim 1, further comprising an excitation filter mounting portion coupled to the second arm, wherein the light source unit is a white lamp, and wherein the excitation filter is mounted on the excitation filter mounting portion and disposed over a light emission surface of the light source unit.

6. The slit lamp microscope configured for capturing fluorescence images of conjunctival goblet cells of claim 1, wherein the second arm is coupled to the main shaft higher than the first arm, and the third arm is coupled to the main shaft higher than the second arm.

* * * * *